United States Patent
Benedini et al.

(10) Patent No.: US 6,753,442 B1
(45) Date of Patent: Jun. 22, 2004

(54) AMORPHOUS NITRIC ESTERS AND THEIR PHARMACEUTICAL COMPOSITIONS

(75) Inventors: Francesca Benedini, Milan (IT); Patrizia Antognazza, Milan (IT)

(73) Assignee: Nicox S.A., Paris (FR)

( * ) Notice: Subject to any disclaimer, the term of this patent is extended or adjusted under 35 U.S.C. 154(b) by 0 days.

(21) Appl. No.: 10/009,741

(22) PCT Filed: Jun. 21, 2000

(86) PCT No.: PCT/EP00/05723

§ 371 (c)(1),
(2), (4) Date: Dec. 17, 2001

(87) PCT Pub. No.: WO01/00563

PCT Pub. Date: Jan. 4, 2001

(30) Foreign Application Priority Data

Jun. 24, 1999 (IT) .......................................... MI99A1402

(51) Int. Cl.$^7$ .......................... C07C 69/76; A01N 37/12
(52) U.S. Cl. .............................. 560/66; 566/23; 514/534
(58) Field of Search ....................... 566/66, 23; 514/534

(56) References Cited

U.S. PATENT DOCUMENTS

| 5,597,847 A | 1/1997 | Matji et al. |
| 5,621,000 A | 4/1997 | Arena et al. |

FOREIGN PATENT DOCUMENTS

| WO | WO 95/30641 | 11/1995 |
| WO | WO 97/16405 | 5/1997 |
| WO | WO 98/57967 | 12/1998 |
| WO | WO 00/44705 | 8/2000 |

*Primary Examiner*—Paul J. Killos
(74) *Attorney, Agent, or Firm*—Arent & Fox PLLC

(57) ABSTRACT

Compounds of formula A—$X_1$—$ONO_2$ (I) in a partially or completely amorphous form and pharmaceutical compositions thereof.

16 Claims, No Drawings

AMORPHOUS NITRIC ESTERS AND THEIR PHARMACEUTICAL COMPOSITIONS

The present invention relates to nitroxy derivatives of the hydroxybenzoic acid in a modified physical form, and the pharmaceutical formulations thereof, said derivatives having general formula

A—X$_1$—NO$_2$ (I)

wherein A is an hydroxybenzoic acid derivative as defined hereunder; X$_1$ is a linking bivalent radical as defined hereunder, said formulations capable to induce in very short times, of the order of 2–2.5 hours, the plasmatic concentration peak of the hydroxybenzoic acid derivative, defined as A.

The compositions of the invention can be used to prepare oral dosage forms suitable to induce a fast beginning of the pharmacological effect.

As well known the pharmacologically active substances when administered per os produce a systemic effect only after having undergone an absorption process through the gastroenteric duct walls. The drug absorption process is a complex phenomenon which depends on various factors, among which drug liposolubility and hydrosolubility. It is difficult to theoretically foresee, in practice it is impossible to know which is the optimal combination of these factors to obtain the maximum absorption peak of the active principle in short times, of about 2–2.5 hours at most.

Generally the therapeutic effect of a drug which shows its activity by systemic route when administered per os depends, in particular, on the following factors:

drug absorption through the gastrointestinal wall,
concentration in the hematic fluid,
possible interaction whith the target tissue.

In particular for the drugs having an antiinflammatory and analgesic activity, an essential feature is the action quickness, i.e. the effect onset has to show in relatively short times after consumption.

The nitroderivative compounds of formula (I), in the unmodified physical form according to the present invention, are known from the patent applications WO 95/30641 and WO 97/16405 in the name of the Applicant. These compounds with respect to the antiinflammatory precursor drugs have a global comparable or higher efficacy, but they have the advantage to show lower side effects. The drawback of these products is that they do not show chemical physical properties such as to allow an haematic peak of maximum absorption in the period of time of 2.5 hours at most. Pharmacokinetic studies carried out by the Applicant using a conventional pharmaceutical formulation for oral use of the nitroderivative compounds of formula (I), not treated as reported in the present invention, have shown that there is no haematic concentration peak in the above mentioned short times, therefore the product does not timely show its therapeutic properties. See the Examples showing that the haematic peak takes place after too long times from the consumption, of about 6 hours.

The need was felt to have available pharmaceutical compositions for oral use, comprising the nitroderivative compounds of formula (I), such as to produce a maximum plasmatic concentration peak ($C_{max}$) in short times, such that $t_{max}$ ($t_{max}$ being the time at which $C_{max}$ occurs) is of about 2.5 hours at most, preferably lower than or equal to 2 hours.

It has been found by the Applicant that it is possible to solve this technical problem with the compounds and formulations thereof for oral use as indicated hereinafter.

An object of the present invention are compounds of formula (I) and pharmaceutical compositions for oral use comprising as active principle said compounds

A—X$_1$—NO$_2$ (I)

wherein
A=R(COX),
X=O, NH, NR$_{1C}$, wherein R$_{1C}$ is a linear or branched C$_1$–C$_{10}$ alkyl, R is selected from the following radicals:

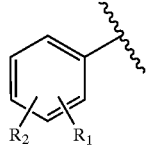
(Ia)

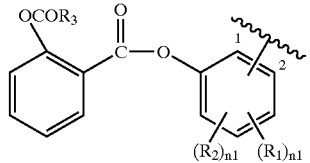
(Ib)

wherein
R$_1$ is a OCOR$_3$ group; wherein R$_3$ is methyl, ethyl or linear or branched C$_3$–C$_5$ alkyl, or the residue of a saturated heterocyclic ring having 5 or 6 atoms, which can be aromatic or completely or partially saturated, said heterocyclic ring containing one or more heteroatoms independently selected between O and N;

R$_2$ is hydrogen, hydroxy, halogen, linear or branched when possible C$_1$–C$_4$ alkyl, linear or branched when possible C$_1$–C$_4$ alkoxyl; linear or branched when possible C$_1$–C$_4$ perfluoroalkyl, for example trifluoromethyl; mono— or di—(C$_1$–C$_4$) alkylamino;

R$_1$ and R$_2$ together are the dioxymethylene group, with the proviso that when X=NH, then Y is ethylene and R$_2$ =H as defined hereinder;

R$_1$ cannot be OCOR$_3$ in position 2 when R$_3$ is methyl;
nI is an integer and is ) or 1.

Preferably in (Ia X=0, R$_1$ is acetoxy and is in ortho position with respect to the -CO- group, R$_2$ hydrogen; preferably in Ib) R$_{3=CH3}$, nI=0; X is equal to O, and the bond of the aromatic ring with the COX group is in the 1 or 2 positions;

X$_1$ is a bivalent linking bridge selected from the following:
YO:
Y=linear or branched when possible C$_1$–C$_{20}$, preferably
C$_2$–C$_5$, alkylene; or
C$_5$–C$_7$ cycloalkylene optionally substituted;

or X$_1$ is selected from the following:

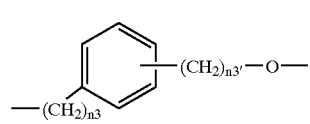
(PAI)

wherein n3 is an integer from 0 to 3, n3' is an integer from 1 to 3;

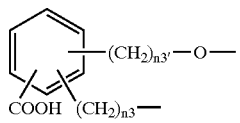

(PAII)

wherein n3 and n3' have the above mentioned meaning;

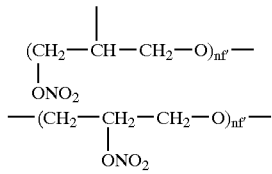

wherein nf' is an integer from 1 to 6, preferably from 1 to 4;

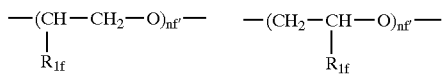

wherein $R_{1f}$=H, $CH_3$ and nf' is as above defined; said compounds of formula (I) being completely or partially in amorphous form.

The amorphization degree can be measured by well known methods such as for example DSC, RX, IR, etc. For partially amorphous it is meant that in the pharmaceutical compositions of the invention the compounds of formula (I) are generally amorphous for at least 5%, preferably 10%, more preferably for at least 80%, as measured by DSC.

The amorphization degree is determined by DSC as variation reduction) of the subtended area of the endothermic melting peak of the active principle. When the amorphization is complete, the melting peak characteristic of the active principle of formula (I) substantially disappears. This means that there is a variation of the enthalpy associated to the melting peak.

A test for measuring the amorphization degree according to the present invention is the following: an amount of nitroderivative of formula (I) is added with hydroxypropyl-β-cyclodextrin in the molar ratio 1:2; 43 g of the compound of formula (I) are dissolved in 5 l of ethyl alcohol; the so obtained organic solution is mixed at room temperature with 5 l of deionized water containing 7% w/v (350 g) of hydroxypropyl-β-cyclodextrin. The hydroalcoholic solution is treated in the spray-drying LabPlant SD-05 Spray-Drying equipment, with an hot air flow at the inlet at the temperature of 60° C., maintaining an air flow such as to allow outlet temperatures of about 45° C.; the crystallinity loss is evaluated on the powder (5–10 mg) by the DSC method and the variation of the peak area is determined by comparing the area with that of the precursor treated under the same conditions without the addition of cyclodextrin.

An indicative test of the crystallinity decrease of the compounds of formula (I) is based on the determination of their dissolution rate in water.

The dissolution rate test is carried out in a dissolving equipment according to United States Pharmacopeia 23 by using a volume of deionized water of 1000 ml. The blade stirrer speed is of 100 rpm and the temperature is 37±0.5° C.

In a little glass vessel an exact amount of each sample is weighed so that it contains an amount of the active principle equal to 30 mg, which is directly introduced in the vessel containing the deionized water. At predetermined times, respectively of 5, 10, 15, 30, 45, 50, 60, 90 and 120 minutes from the beginning of the test, the amount of the nitroderivative compound passed in solution is determined, by measuring the concentration w/v (weigh/volume) thereof by UV spectrophotometry at the wave length of 235 nm, using a calibration line. The data are expressed as percentage of nitroderivative compound passed in solution in connection with the time. The amount of the compound of formula (I) passed in solution at the time of 10 minutes is at least about 10 times higher with respect to that of the nitroderivative compound not in amorphous form.

As said, the formulations of the invention are surprisingly and unexpectedly capable to induce in very short times, in the order of 2–2.5 hours, the plasmatic concentration peak of the hydroxybenzoic acid derivative A.

Preferably in the compounds of formula (I) R=(Ia), X=O and $X_1$ is the aromatic radical of formula (PAI) wherein n3'=1 and n3=0; said preferred compounds having the following general formula (IA1):

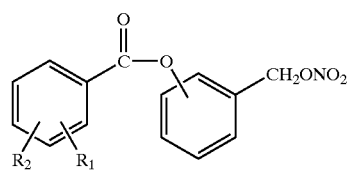

(IA1)

wherein $R_1$ and $R_2$ are as above defined.

The ester of formula (Ia1) wherein the nitroxymethyl group is on the aromatic ring in meta position, or position 3, with respect to the carbon atom bound to the oxygen of the ester group, is preferred.

The Applicant has surprisingly and unexpectedly found that when the nitroderivatives of formula (I) are present in the pharmaceutical compositions of the invention in a completely or partially amorphized form, in consequence of gastrointestinal absorption, high plasmatic concentrations are obtained in very short times, the maximum plasmatic concentration peak is obtained in a period of time of 2.5 hours at most.

The partially or completely amorphized nitroderivative compounds of formula (I) are obtainable by treating the nitroderivatives with one or more excipients, capable to amorphize said nitroderivatives.

The techniques used for the amorphization are for example co-grinding, kneading, spray-drying, lyophilization, preferably spray-drying and co-grinding.

In particular in the spray-drying technique the active principle is dissolved in a solvent, for example alcohols, and the so obtained organic solution is mixed at room temperature with a solution or suspension of the excipient capable to give amorphization of the compounds of formula (I). The solution or suspension resulting after mixing is treated in a spray-drying equipment. For this and the other techniques see the specific Examples.

Excipients preferably belong to one or more classes mentioned hereinafter: $C_5$–$C_6$ polyalcohols, mono- and disaccharides and their derivatives, oligosaccharides containing from 3 to 10 saccharide units and their derivatives, polysaccharides, their derivatives including their salts, cyclodextrins and their derivatives, non cyclic cyclodextrin analogues, for example non cyclic derivatives of β-cyclodextrin, polymers and copolymers of vinyl-based monomeric units, and/or containing a carboxylic function, or (meth)acrylic monomers.

Examples of $C_5$–$C_6$ polyalcohols are sorbitol, mannitol; examples of monosaccharides and their derivatives are glucose, fructose, mannose, galactose glucosamine; example of disaccharides are lactose, saccharose, maltose etc; examples of polysaccharides and their derivatives are microcrystalline cellulose, hydroxypropylcellulose, hydroxyethylcellulose hydroxymethylcellulose, methylcellulose, ethylcellulose carboxymethylcellulose, and their salts, preferably sodium and calcium salts, and their crosslinked forms, cellulose acetate, cellulose acetophthalate and their ethers, for ex. cellulose phthalate hydroxypropylmethyl ether, starch and derivatives such as for example sodium carboxymethylstarch, soluble starch, pregelled starch; examples of cyclodextrins and derivatives thereof are dimethyl-β-cyclodextrin, 2-hydroxy-ethyl-β-cyclodextrin, 2-hydroxypropyl-β-cyclodextrin, 3-hydroxypropyl-β-cyclodextrin, trimethyl-β-cyclodextrin.

An object of the present invention are the pharmaceutical compositions for oral use containing as active principle the partially or completely amorphized compounds of formula (I) and comprising at least one of the above mentioned excipients.

It has been found by the Applicant that the formulations of the invention show an improved dissolution rate in water, determined by the above described dissolution test.

In the compositions according to the present invention the ratio between the amount by weight of nitroderivatives of formula (I) and that of the excipients capable to amorphize the nitroderivatives is generally in the range 1:20 and 1:0.5, preferably 1:0.7 and 1:10.

As said, the formulations for oral use of the present invention are capable to induce in very short times, of the order of 2–2.5 hours, the plasmatic concentration peak of the hydroxybenzoic acid derivative as defined in A, and it has also been found that they are capable to produce the following pharmacokinetic effects:

- to increase the plasmatic $C_{MAX}$ (maximum concentration) of the hydroxybenzoic acid derivative as defined in A, after single administration, with respect to the untreated (not amorphized) product according to the present invention;
- to increase of at least 20%, preferably of 50%, the area substended from the curve of the plasmatic concentrations in the range 0–3.5 hours from the administration.

When in the partially or completely amorphized product of formula (I) R=(Ia) the hydroxybenzoic acid derivative as defined in A is the salicylic acid (see the Examples).

The nitroderivative compounds of formula (I) wherein R is a radical of formula Ia) or Ib) are obtainable according to the known methods in the prior art. See for example the methods described in the patent applications in the name of the Applicant WO 95/30641, WO 97/16405, or in the international patent application PCT/EP00/00353.

The following examples illustrate the invention without limiting the scope thereof.

EXAMPLES

A) Characterization of the Compound of Formula (I) by DSC

The characterization is exemplified for the 3-(nitroxymethyl)phenyl ester of the acetylsalicylic acid, the substance used in the examples described hereinafter, which has been obtained according to Example 1 of the international patent application PCT/EP00/00353.

The specific melting enthalpy ΔH (Joule/g) of the product as such and of the product treated with processes able to decrease the crystallinity (formulation) thereof, is determined by DSC analysis.

The percent crystallinity loss is evaluated by the following equation:

$$\% \text{ crystallinity loss} = \frac{\Delta H_{\text{drug as such}} - \Delta H_{\text{treated drug}}}{\Delta H_{\text{drug as such}}} \times 100$$

The scanning parameters adopted for the DSC analysis are the following:

Scanning range: from 30° C. min. to 330° C. max

Scanning rate: 10 K/min

The DSC trace of the ester as such shows a melting endothermic peak at T=64.7° C. with respective ΔH=99,81 Joule/g.

B) Dissolution Rate Test of the Compound of Formula (I) 3-(nitroxymethyl)phenyl Ester of the Acetylsalicylic Acid The dissolution rate of 3-(nitroxymethyl)phenyl ester of the acetylsalicylic acid as such and in the preparations containing it according to the examples described hereinafter, has been carried out in a dissolving equipment according to USP (United States Pharmacopeia) XXIII.

The test is carried out by using a volume of deionized water of 1000 ml. The angle rate of the blade stirrer is of 100 rpm and the temperature of 37±0.5° C.

In a little glass vessel an exact amount of each preparation to be tested is weighed so that it contains an amount of the active principle equal to 30 mg, which is directly introduced in the vessel. At predetermined times, respectively of 5, 10, 15, 30, 45, 50, 60, 90 and 120 minutes from the beginning of the test the amount of the compound passed in solution is determined, by measuring the concentration w/v thereof by UV spectrophotometry at the wave length of 235 nm, using a calibration line. The data are expressed as percentage of active principle passed in solution in connection with the time.

Example 1

Comparative

Dissolution Rate of 3-(nitroxymethyl)phenyl Ester of the Completely Crystalline Acetylsalicylic Acid The recrystallized product from isopropanol results completely crystalline, and by DSC analysis it shows an endothermic peak at T=64.7° C. with ΔH 99.81 J/g, and an exothermic decomposition peak at T=220° C. with ΔH 879.47 J/g.

30 mg of said compound are transferred into the equipment for determining the dissolution rate. In Table 1 the percentages of the compound passed in solution, measured at the times indicated in the above described test, are reported. After 10 minutes the amount of active principle passed in solution is 0.3%.

Example 2

Obtainment of 3-(nitroxymethyl)phenyl ester of the completely amorphous acetylsalicylic acid by spray-drying treatment of the compound in admixture with hydroxypropyl-β-cyclodextrin in the ratio by weight compound:cyclodextrin 1:8.33 corresponding to a molar ratio of 1:2.

43 g of the compound are dissolved in 5 l of ethyl alcohol. The so obtained organic solution is mixed at room temperature with 5 l of deionized water containing 7% w/v (350 g) of hydroxypropyl-β-cyclodextrin. The hydroalcoholic solution is treated in the spray-drying LabPlant SD-05 Spray-Drying equipment, with a hot air flow at the inlet at the temperature of 60° C., maintaining an air flow such as to allow outlet temperatures of about 45° C.

The compound crystallinity loss, measured on the so obtained powder according to the DSC method is of 100%. In fact in the DSC trace the melting endothermic peak is absent.

An amount of the powder corresponding to 30 mg of active principle is weighed and transferred into the equipment for determining the dissolution rate. In Table 1 the percentages of the compound passed in solution, measured at the times indicated in the above described dissolution test, with respect to the weighed amount, are reported. After 10 minutes the active principle % passed in solution is 32%.

Example 3

Obtainment of 3-(nitroxymethyl)phenyl ester of the partially amorphous acetylsalicylic acid by spray-drying treatment of the compound in admixture with lactose in the ratio 1 (compound):9 (lactose) by weight.

10 g of the compound are dissolved in 1.5 l of ethyl alcohol. The obtained organic solution is mixed with 1.5 l of deionized water containing 6% w/v (90 g) of lactose. The hydroalcoholic solution is treated in the spray-drying equipment, operating with an hot air flow at the inlet of 70° C., maintaining an air flow such as to allow outlet temperatures of about 50° C.

The crystallinity loss, measured according to the DSC method on the so obtained powder is of 87% ($\Delta H$ 12.58 J/g).

An amount of powder equal to 30 mg of active principle is weighed and transferred into the equipment for determining the dissolution rate. In Table 1 the percentages of the compound passed in solution, measured at the times indicated in the above described dissolution test, are reported. After 10 minutes the % of active principle passed in solution is 30%.

Example 3A

Obtainment of 3-(nitroxymethyl)phenyl ester of the partially amorphous acetylsalicylic acid by the spray-drying treatment of the compound in admixture with microcrystalline cellulose in the 1:0.7 ratio.

10 g of the compound are dissolved in 1.5 l of ethyl alcohol. To the solution 0.670 liters of a 1% w/v (weight/volume) aqueous suspension of microcrystalline cellulose (Avicel PH 101) are added. The suspension is submitted to spray-drying, operating with an air temperature at the inlet of 70° C. and maintaining an air flow such as to allow outlet temperatures of about 50° C.

An amount of powder equal to 30 mg of active principle is weighed and transferred into the equipment for determining the dissolution rate. In Table 1 the percentages of the compound passed in solution, measured at the times indicated in the above described dissolution test, are reported. After 10 minutes the % of active principle passed in solution is of 9.4%. The crystallinity loss is 10%.

Example 3B

Obtainment of 3-(nitroxymethyl)phenyl ester of the partially amorphous acetylsalicylic acid by treatment by co-milling in admixture with microcrystalline cellulose and sodium lauryl sulphate in ratios by weight active principle:microcrystalline cellulose:surfactant equal to 1:0.5:0.1.

10 g of the active principle are mixed in a mortar with 1 g of sodium lauryl sulphate for 5 minutes and subsequently with 5 g of microcrystalline cellulose. The powder mixture is forcedly co-milled with a pestle for 30 minutes.

The dissolution test is carried out by using 48 mg of the obtained mixture, equal to 30 mg of the active principle.

The percentages of the compound passed in solution, at the times indicated in the above described dissolution test, are reported in Table 1. The % of active principle passed in solution after 10 minutes is equal to 4.8%.

The powder DSC analysis shows a crystallinity loss of the active principle of 6%.

Example 4

Obtainment of 3-(nitroxymethyl)phenyl ester of the partially crystalline acetylsalicylic acid by spray-drying treatment of the compound in admixture with lactose in the ratio 1 (compound):4 (lactose) by weight.

10 g of the compound are dissolved in 1.5 l of ethyl alcohol. The obtained organic solution is mixed with 0.75 l of deionized water containing 6% w/v (45 g) of lactose. The hydroalcoholic solution is treated in the spray-drying equipment, operating with an hot air flow at the inlet of 70° C., maintaining an air flow such as to allow outlet temperatures of about 50° C.

The crystallinity loss, evaluated on the so obtained powder according to the DSC method, is of 83% ($\Delta H$ 16.44 J/g).

An amount at the obtained powder corresponding to 30 mg of active principle is weighed and transferred into the equipment for determining the dissolution rate. The percentages of the compound passed in solution, at the times mentioned in the dissolution test indicated in B), are reported in Table 1. After 10 minutes the active principle % passed in solution is of 17.1%.

Example 5

Obtainment of 3-(nitroxymethyl)phenyl ester of the partially amorphous acetylsalicylic acid by co-milling treatment of the compound in admixture with hydroxypropyl-β-cyclodextrin in the ratio compound:cyclodextrin of 1:4.16 by weight corresponding to a molar ratio 1:1.

10 g of the compound are mixed with 41.6 g of cyclodextrin. The mixture is co-milled in a mortar for 30 minutes.

The crystallinity loss, evaluated on the so obtained powder according to the DSC method, is of 43% ($\Delta H$ 56.5 J/g).

An amount of the obtained powder corresponding to 30 mg of active principle is weighed and transferred into the equipment for determining the dissolution rate. The percentages of the compound passed in solution, at the times mentioned in the dissolution test indicated in B), are reported in Table 1. After 10 minutes the active principle % passed in solution is of 6.9%.

Example 6

Obtainment of 3-(nitroxymethyl)phenyl ester of the partially amorphized acetylsalicylic acid by treating the compound by kneading in admixture with lactose in the ratio 1 compound:9 lactose by weight.

5 g of the compound are directly mixed with 45 g of lactose. The mixture is kneaded with 10 ml of ethanol 50% in water and then let dry under vacuum of the water pump at room temperature for 24 hours. The dried product is sieved by a sieve with 600 μm meshes before the analyses.

The crystallinity loss, measured on the so obtained powder according to the DSC method, is of 7% ($\Delta H$ 92.34 J/g).

An amount of the obtained powder corresponding to 30 mg of active principle is weighed and transferred into the equipment for determining the dissolution rate. The percentages of the compound passed in solution, at the times mentioned in the dissolution test indicated in B), are reported in Table 1. After 10 minutes the % of active principle passed in solution is of 11.5%.

Example 6A

Example 6 was repeated but using a mixture comprising also hydroxypropyl-β-cyclodextrin, in ratios active principle lactose:hydroxypropyl-β-cyclodextrin 1:0.5:0.2 by weight.

1000 g of the active principle are mixed with 500 g of lactose and 200 g of hydroxypropyl-β-cyclodextrin. The mixture is kneaded by a mechanical kneader with 100 ml of a solution 3% w/v of polyvinylpyrrolidone in water/isopropyl alcohol 1:1, operating by progressive additions.

The kneading is extruded through a granulator die, and dried in a drier at the temperature of 40° C. The dried granulate is passed through the mesh of an oscillating granulator, in order to uniform the granulometry.

An amount of the obtained powder corresponding to 30 mg of active principle is weighed-and transferred into the equipment for determining the dissolution rate. The percentages of the compound passed in solution, at the times indicated in the dissolution test described in B), are reported in Table 1. After 10 minutes the % of active principle passed in solution is of 15.6%. The crystallinity loss is of 39.4%.

Example 7

Comparative

Spray-drying of the Active Principle as Such 16 g of 3-(nitroxymethyl)phenyl ester of the acetylsalicylic acid are dissolved in 3 l of a mixture of ethyl alcohol/water 80/20. The hydroalcoholic solution is treated in the spray-drying equipment with an hot air flow at the inlet of 60° C., maintaining an air flow such as to allow outlet temperatures of about 45° C.

The DSC analysis on the obtained powder shows that the compound is in a completely crystalline form (ΔH 100.5 J/g).

30 mg of powder of the active principle is weighed and transferred into the equipment for determining the dissolution rate. The percentages of the compound passed in solution, measured at the times indicated in the dissolution test described in A), are reported in Table 1. After 10 minutes the % of active principle passed in solution is of 0.5%, therefore not substantially different from that obtained in the dissolution test of the active principle as such (ref. Example 1).

Example 8

Comparative

Preparation of Tablets According to the Prior Art Containing: 300 mg of 3-(nitroxymethyl)phenyl Ester of the Acetylsalicylic Acid, 143.7 mg of Microcrystalline Cellulose, 3 mg of Talc, 3 mg of Magnesium Stearate and 0.3 mg of Silica 300 g of active principle are mixed in a mortar with 0.3 g of colloidal silica, 143.7 g of microcrystalline cellulose added in aliquots, according to the subsequent dilution method. Then 3 g of talc are added. The mixture is transferred into a powder mixer (Turbula) and mixed for 10 minutes. 3 g of magnesium stearate are added and mixing is continued for futher 5 minutes. The powder mixture is directly compressed by a rotative compressor (Officine Ronchi) equipped with bombed punches (9.5 mm diameter; 9 mm bending radius) obtaining tablets having an average weight of 450 mg and an average strenght at break of 10 kg. The so obtained tablets are crumbled in a mortar until obtaining a powder capable to pass the 200 µm meshes of a sieve. An amount of the obtained powder corresponding to 30 mg of active principle is weighed and transferred into the equipment for determining the dissolution rate. The percentages of the compound passed in solution, at the times indicated in the dissolution test described in B), are reported in Table 1. After 10 minutes the active principle % passed in solution is of 0.34%.

The DSC analysis does not show any evidence of the active principle amorphization due to compacting.

Tests in vivo

Example 9

Pharmacokinetic in the animal by using the pharmaceutical composition according to the present invention described in Example 3B.

A single dose of 80 mg/Kg, equal to 50 mg/Kg of active principle, of the pharmaceutical composition (powder) of Example 3B in aqueous suspension (5 ml/Kg) was administered by os to a group of 10 rats weighing 180–200 g.

Samples of 0.5 ml of blood were taken from the caudal vein of the animals after 0.5, 1, 1.5, 2, 4, 8, 12 and 24 hours from administration.

The samples are transferred into heparinised test tubes and centrifuged for 15 minutes at room temperature. A 100 µl aliquot of serum was added with 25 µl of an internal standard solution (prepared by dissolving 10 mg of naproxene in 100 ml of acetonitrile). The sample is injected in a HPLC Hewlett Packard series 1050 equipment, having a variable wave length detector, pump, self-sampler with a 5 µm ODS 2 (10×0.46 cm) column connected in series to a 5 µm ODS 2 (C18—250×4 mm) column. The moving phase is constituted by acetonitrile/acetic acid 3% in the ratio 60/40 by volume. The flow is 0.8 ml/min. All the analyses have been carried out at room temperature and the measures have been effected at the wave length of 234 nm. The $C_{Max}$ value is 61.7 µg/ml at the time of 2 hours.

Example 10

Comparative

Pharmacokinetic in the Animal by Using the Pharmaceutical Composition Described in Example 8

A single dose of 75 mg/Kg, equal to 50 mg/Kg of active principle, of the powder obtained from the crumbled tablets described in Example 8 in aqueous suspension (5 ml/Kg) was administered by os to a group of 10 rats weighing 180–200 g.

Samples of 0.5 ml of blood were taken from the caudal vein of the animals after 1.5, 3, 6, 12 and 24 hours from administration. One proceeds as described in the previous Example 8. The $C_{Max}$ value is 53.2 µg/ml at the time of 6 hours.

TABLE 1

Dissolution test on the samples of the active principle of the Examples

% by weight of the active principle passed in solution

| Time (minutes) | Ex. 1 Comp. | Ex. 2 | Ex. 3 | Ex. 3A | Ex. 3B | Ex. 4 | Ex. 5 | Ex. 6 | Ex. 6A | Ex 7 Comp. | Ex. 8 comp. |
|---|---|---|---|---|---|---|---|---|---|---|---|
| 0 | 0.0 | 0.0 | 0.0 | 0.0 | 0.0 | 0.0 | 0.0 | 0.0 | 0.0 | 0.0 | 0.0 |
| 5 | 0.1 | 29.9 | 28.7 | 5.1 | 2.7 | 14.2 | 3.8 | 6.9 | 10.8 | 0.3 | 0.2 |
| 10 | 0.3 | 32.4 | 29.3 | 9.4 | 4.8 | 17.1 | 6.9 | 11.5 | 15.6 | 0.5 | 0.3 |
| 15 | 0.4 | 33.0 | 29.2 | 12.3 | 6.4 | 18.7 | 9.0 | 14.3 | 18.1 | 0.8 | 0.5 |
| 30 | 0.8 | 32.5 | 28.1 | 16.4 | 9.3 | 20.2 | 11.8 | 18.1 | 21.3 | 1.5 | 0.9 |
| 45 | 1.2 | 32.5 | 27.6 | 19.1 | 11.4 | 21.6 | 13.9 | 20.7 | 23.0 | 2.2 | 1.4 |
| 60 | 1.6 | 32.3 | 27.2 | 20.9 | 12.9 | 22.6 | 15.6 | 22.5 | 23.9 | 2.7 | 1.9 |
| 90 | 2.4 | 31.9 | 26.4 | 22.4 | 15.0 | 23.6 | 17.6 | 24.0 | 24.8 | 4.0 | 2.7 |
| 120 | 3.1 | 31.7 | 26.3 | 23.5 | 16.6 | 24.5 | 19.4 | 25.1 | 25.6 | 5.2 | 3.7 |

What is claimed is:

1. A method for preparing a pharmaceutical formulation for oral administration comprising a compound of formula (I)

$$A-X_1-NO_2 \quad (I)$$

having a completely amorphous or partially amorphous form, said method comprising the following steps:
  admixing the compound of formula (I) with at least one excipient capable of at least partially amorphizing the compound; and
  at least partially amorphizing the obtained mixture;
wherein in formula (I)
  A=R(COX)
  X=O, NH, NR$_{1c}$, wherein R$_{1c}$ is a linear or branched C$_1$–C$_{10}$ alkyl, R is selected from the following radicals;

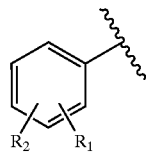
(Ia)

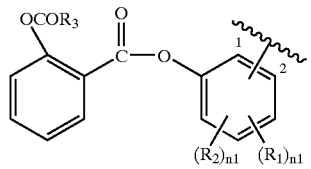
(Ib)

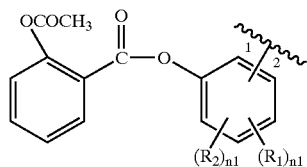
(Ib)

wherein:
  R$_1$ is a OCOR$_3$ group; wherein R$_3$ is methyl, ethyl or a linear or branched C$_3$–C$_5$ alkyl, or the residue of a saturated heterocyclic ring having 5 or 6 atoms, which can be aromatic or completely or partially saturated, said heterocyclic ring containing one or more heteroatoms independent selected from O and N and S;
  R$_2$ is hydrogen, hydroxy, halogen, linear or branched C$_1$–C$_4$ alkyl, linear or branched C$_1$–C$_4$ alkoxyl; linear or branched C$_1$–C$_4$ perfluoroalkyl; mono- or di- (C$_1$–C$_4$) alkylamino;
  R$_1$ and R$_2$ together are the dioxymethylene group, with the proviso that when X=NH, then Y is ethylene and R$_2$=H as defined hereunder;
  R$_1$ cannot be OCOR$_3$ in position 2 when R$_3$ is methyl;
  nl is an integer and is 0 or 1;
  X$_1$ is a bivalent linking bridge selected from the following YO:
    Y=linear or branched C$_1$–C$_{20}$ alkylene; or a substituted or unsubstituted C$_5$–C$_7$ cycloalkylene;
  or X$_1$ is selected from the following:

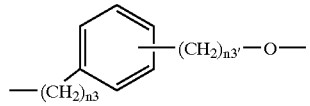
(PAI)

wherein n3 is an integer from 0 to 3, n3' is an integer from 1 to 3;

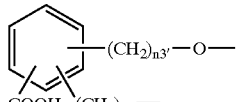
(PAII)

wherein n3 and n3' have the above mentioned meaning:

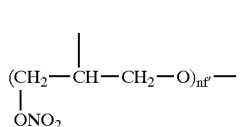

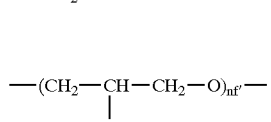

wherein nf is an integer from 1 to 6;

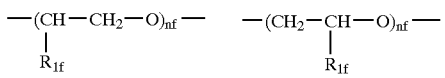

wherein $R_{1f}$=H, $CH_3$ and nf' is as above defined.

2. The method according to claim 1 wherein the compound of formula (I) is amorphous for at least 5%, as measured by DSC.

3. The method according to claim 1 wherein the compound of formula (I) is amorphous for at least 80% as measured by DSC.

4. The method according to claim 1 wherein the compound of formula (I) is completely amorphous.

5. The method according to claim 1, wherein in formula (I), R=(Ia).

6. The method according to claim 1, wherein in formula (I), R=(Ia), X=O and $X_1$ is the aromatic radical of formula (PAI) wherein n3'=1 and n3=0.

7. The method according to claim 1, wherein the compound of formula (I) is 3-(nitrooxymethyl)phenyl ester of acetylsalicylic acid.

8. The method according to claim 1, wherein the at least one excipient is selected from the group consisting of: $C_5$–$C_6$ polyalcohols, mono and disaccharides and their derivatives, oligosaccharides containing from 3 to 10 saccharide units and their derivatives, polysaccharides and their derivatives including salts, cyclodextrins and their derivatives, non cyclic cyclodextrin analogues including non cyclic derivatives of β-cyclodextrin, polymers and copolymers of vinyl-based monomeric units, and/or containing a carboxylic function, or (meth)acrylic monomers.

9. The method according to claim 1, wherein the ratio between the amount by weight of the compound of formula (I) and that of the at least one excipient is in the range 1:20 and 1:0.5.

10. The method according to claim 1, wherein the ratio between the amount by weight of the compound of formula (I) and that of the at least one excipient is in the range 1:10 and 1:0.7.

11. The method according to claim 1, wherein the amorphizing is performed by at least one of the following: co-grinding, kneading, spray-drying, and lyophilization.

12. The method according to claim 1, wherein the amorphizing is performed by co-grinding.

13. A method of treating inflammation, said method comprising administering to a patient in need thereof an anti-inflammatory effective amount of a pharmaceutical composition comprising a compound of formula (I) A—$X_1$—$NO_2$ having a completely amorphous or partially amorphous form, wherein in formula (I):

A=R(COX),

X=O, NH, $NR_{1c}$, wherein $R_{1c}$ is a linear or branched $C_1$–$C_{10}$ alkyl, R is selected from the following radicals:

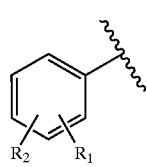
(Ia)

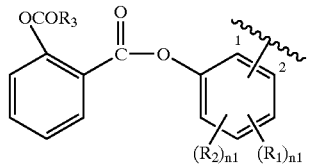
(Ib)

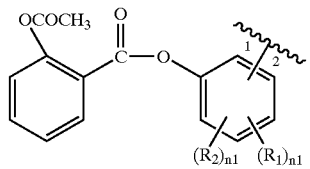
(Ib)

wherein:

$R_1$ is a $OCOR_3$ group; wherein $R_3$ is methyl, ethyl or a linear or branched $C_3$–$C_5$ alkyl, or the residue of a saturated heterocyclic ring having 5 or 6 atoms, which can be aromatic or completely or partially saturated, said heterocyclic ring containing one or more heteroatoms independent selected from O and N and S;

$R_2$ is hydrogen, hydroxy, halogen, linear or branched $C_1$–$C_4$ alkyl, linear or branched $C_1$–$C_4$ alkoxyl; linear or branched $C_1$–$C_4$ perfluoroalkyl, mono- or di-($C_1$–$C_4$) alkylamino; or $R_1$ and $R_2$ together are the dioxymethylene group, with the proviso that when X=NH, then Y is ethylene and $R_2$=H as defined hereunder;

$R_1$ cannot be $OCOR_3$ in position 2 when $R_3$ is methyl;

n1 is an integer and is 0 or 1;

$X_1$ is a bivalent linking bridge selected from the following: YO:

Y=linear or branched $C_1$–$C_{20}$ alkylene; or a substituted or unsubstituted $C_5$–$C_7$ cycloakylene;

or $X_1$ is selected from the following:

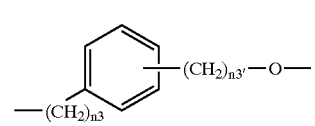
(PAI)

wherein n3 is an integer from 0 to 3, n3' is an integer from 1 to 3;

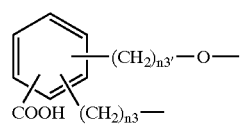
(PAII)

wherein n3 and n3' have the above mentioned meaning:

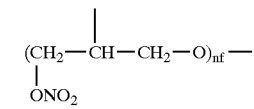

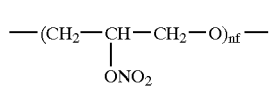

wherein nf' is an integer form 1 to 6;

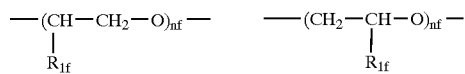

wherein $R_{1f}$=H, $CH_3$ and nf' is as above defined.

14. The method according to claim 13, wherein the compound of formula (I) is amorphous for at least 5%, as measured by DSC.

15. The method according to claim 13, wherein the compound of formula (I) is amorphous for at least 80%, as measured by DSC.

16. The method according to claim 13, wherein the compound of formula (I) is completely amorphous.

* * * * *

UNITED STATES PATENT AND TRADEMARK OFFICE
CERTIFICATE OF CORRECTION

PATENT NO.    : 6,753,442 B1
DATED         : June 22, 2004
INVENTOR(S)   : Benedini et al.

It is certified that error appears in the above-identified patent and that said Letters Patent is hereby corrected as shown below:

Column 2,
Line 45, please change "X=0" to -- X=O --
Line 47, please change "$R_{3=CH3}$" to -- $R_3=CH_3$ --

Column 11,
Lines 53-59, please delete formula (Ib)

Column 14,
Lines 11-18, please delete formula (Ib)

Signed and Sealed this

Seventh Day of December, 2004

JON W. DUDAS
*Director of the United States Patent and Trademark Office*